US008043651B2

(12) United States Patent
O'Connor et al.

(10) Patent No.: US 8,043,651 B2
(45) Date of Patent: Oct. 25, 2011

(54) SYSTEM AND METHOD FOR COATING A MEDICAL DEVICE

(75) Inventors: Tim O'Connor, County Galway (IE); LiJuan He, Bolton, MA (US); Aiden Flanagan, County Galway (IE); Anthony Malone, County Galway (IE); Barry Heaney, County Galway (IE); Dave McMorrow, Galway City (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1037 days.

(21) Appl. No.: 11/876,377

(22) Filed: Oct. 22, 2007

(65) Prior Publication Data

US 2008/0107794 A1 May 8, 2008

Related U.S. Application Data

(60) Provisional application No. 60/856,603, filed on Nov. 2, 2006.

(51) Int. Cl.
*A61L 33/00* (2006.01)

(52) U.S. Cl. .............. 427/2.1; 29/516; 623/1; 427/2.24; 427/2.25

(58) Field of Classification Search ........ 623/1; 29/516; 427/2.1
See application file for complete search history.

(56) References Cited

U.S. PATENT DOCUMENTS 6,125,523 A * 10/2000 Brown et al. .................. 29/516
6,360,577 B2 3/2002 Austin
2005/0074544 A1 4/2005 Pacetti et al.

FOREIGN PATENT DOCUMENTS

GB 2107219 * 4/1983
WO WO 2005/091834 * 6/2005
WO 2005/091834 10/2005
WO 2005/091834 A2 10/2005

OTHER PUBLICATIONS

Partial International Search Report, PCT/US2007/022405, Aug. 8, 2008.
International Search Report and Written Opinion of the International Searching Authority, from PCT/US2007/022405, mailed Mar. 2, 2009.

* cited by examiner

*Primary Examiner* — Dah-Wei Yuan
*Assistant Examiner* — Andrew Bowman
(74) *Attorney, Agent, or Firm* — Vidas, Arrett & Steinkraus

(57) ABSTRACT

A method and device for coating a medical device, such as a stent, including rolling the stent against a ribbon or gravure roll impregnated with coating material. The ribbon and gravure roll may include a recessed pattern matching a strut pattern of the stent. The stent may also be rolled against a plate or cylinder while coating material is forced onto the stent through a pattern of holes or openings in the plate or cylinder matching a strut pattern of the stent.

12 Claims, 11 Drawing Sheets

SYSTEM AND METHOD FOR COATING A MEDICAL DEVICE

RELATED APPLICATIONS

This application claims benefit of U.S. Provisional Application No. 60/856,603, filed Nov. 2, 2006, which is incorporated herein in its entirety.

FIELD OF THE INVENTION

The present invention relates to medical devices. More particularly, the present invention relates to a method of coating a medical device, a system for coating a medical device, and a medical device produced by the method.

BACKGROUND INFORMATION

Medical devices may be coated so that the surfaces of such devices have desired properties or effects. For example, it may be useful to coat medical devices to provide for the localized delivery of therapeutic agents to target locations within the body, such as to treat localized disease (e.g., heart disease) or occluded body lumens. Localized drug delivery may avoid some of the problems of systemic drug administration, which may be accompanied by unwanted effects on parts of the body which are not to be treated. Additionally, treatment of the afflicted part of the body may require a high concentration of therapeutic agent that may not be achievable by systemic administration. Localized drug delivery may be achieved, for example, by coating balloon catheters, stents and the like with the therapeutic agent to be locally delivered. The coating on medical devices may provide for controlled release, which may include long-term or sustained release, of a bioactive material.

Aside from facilitating localized drug delivery, medical devices may be coated with materials to provide beneficial surface properties. For example, medical devices are often coated with radiopaque materials to allow for fluoroscopic visualization while placed in the body. It is also useful to coat certain devices to achieve enhanced biocompatibility and to improve surface properties such as lubriciousness.

Metal stents may be coated with a polymeric coating that may contain a dissolved and/or suspended bioactive agent. The bioactive agent and the polymeric coating may be dissolved in a solvent mix and spray coated onto the stents, for example, by gas assist atomized spray coating. The solvent may then evaporate to leave a dry coating on the stent.

Drawbacks to gas assist atomized coating include its low material transfer efficiency and the presentment of polymer and drug to the inside of the device being coated, such as the inside surface of a stent. Another drawback to gas assist atomized coating includes the resulting high degree of shear to the coating solution, which makes the use of shear sensitive coating materials impossible. Webbing may also present a problem, such as webs of the coating between stent struts.

There is therefore a need for alternative coating methods for medical devices.

SUMMARY OF THE INVENTION

In an exemplary embodiment of the present invention, a ribbon or film is used to impart a therapeutic coating onto an implantable medical device, such as a stent. The stent to be coated is rolled against a drug or drug and polymer impregnated ribbon. The flexibility of the ribbon or film allows it to conform to an outside surface of the stent and, therefore, provides for a consistent coating even for those stents that do not form a true cylinder.

As a preliminary step, a pin may be disposed within the stent and it may be rolled between, for example, two rigid flat plates so as to remove bends in the stent struts.

In another exemplary embodiment of the present invention, a patterned gravure roll is used to impart a coating onto an outside surface of an implantable medical device, such as stent. An outside surface of the roll may be configured to include a pattern matching that of the stent so as to avoid webbing between the stent struts and to increase material transfer efficiency. Use of the patterned gravure roll also provides for a low shear process, which is useful for shear sensitive materials.

In another exemplary embodiment of the present invention, a plate having stent shaped cut outs or a coated screen having stent-shaped openings in the coating may be used to impart a coating onto an outside surface of an implantable medical device, such as stent. A blade or squeegee over the plate or screen may be moved relative to the plate or screen so as to force coating material through the cut-outs or openings onto the stent, which is located directly below the plate or screen and rotates as the plate or screen is moved transversely. The plate or screen may also be rolled into a drum or cylinder so as to provide for a higher throughput coating process. In such a case, the coating material and squeegee may be located inside the drum or cylinder, which itself is configured to roll directly against the stent. Alternatively, instead of the stent shaped cut outs, the cut outs may be rectangular so that the screen can be used like a gravure roller but with positive displacement provided by the squeegee.

The screen may be coated using a screen printing process, which is used very successfully in the electronics industry to impart coatings of very accurate thickness to various substrates. An example of this is the application of conductive and resistive coatings to ceramic substrates in the manufacture of trimming potentiometers. This is generally carried out on flat substrates but can also be used for round or cylindrical components.

Another medical device coating apparatus according to an exemplary embodiment of the present invention includes a ribbon, impregnable with a coating material, and a fixture maintaining contact between a medical device and the ribbon and moving at least one of the medical device and the ribbon relative to the other of the medical device and the ribbon so as to apply the coating material to the medical device.

In an exemplary embodiment of the invention, the fixture generates relative movement between the medical device and ribbon by at least one of (i) rolling the medical device on the ribbon, (ii) rolling the ribbon on the medical device, (iii) rolling the medical device and the ribbon against each other, and (iv) wrapping the ribbon around the medical device.

In an exemplary embodiment of the invention, the ribbon conforms to an outside surface of the medical device.

In an exemplary embodiment of the invention, the fixture includes one of (i) a pin disposed within the medical device, and (ii) a drive belt contacting an outside surface of the medical device.

In an exemplary embodiment of the invention, the medical device coating apparatus includes a cylinder in rolling contact with the ribbon such the medical device is squeezed between the cylinder and one of the pin and the drive belt.

In an exemplary embodiment of the invention, the medical device coating apparatus includes a coating material reservoir through which the ribbon is passed before rolling against the medical device.

In an exemplary embodiment of the invention, the medical device coating apparatus includes a source of coating material and a spray device configured to apply the coating material to a surface of the ribbon.

In an exemplary embodiment of the invention, the medical device coating apparatus includes a vacuum configured to evacuate gas from the ribbon prior to application of the coating material.

In an exemplary embodiment of the invention, the medical device coating apparatus includes a heater configured to heat at least one of the ribbon and the coating material.

In an exemplary embodiment of the invention, a surface speed of the ribbon is different than a surface speed of the medical device.

In an exemplary embodiment of the invention, the ribbon is at least partially porous so as to allow for impregnation of the coating material.

In an exemplary embodiment of the invention, the ribbon has a recessed pattern matching a strut pattern of the stent.

Another medical device coating apparatus according to an exemplary embodiment of the present invention includes: (i) a roll having a recessed pattern on an outer surface, the roll at least partially impregnable with a coating material, the recessed pattern matching a pattern of a medical device; and (ii) a fixture configured to maintain the medical device in rolling contact with the roll, whereby rolling of the roll and the medical device against each other transfers coating material from the recessed pattern on the roll to an outer surface of the medical device.

In an exemplary embodiment of the invention, the medical device coating apparatus includes a heater configured to heat at least one of the coating material and the roll.

In an exemplary embodiment of the invention, the medical device coating apparatus includes a reservoir of the coating material, the roll at least partially immersed in the reservoir.

In an exemplary embodiment of the invention, the fixture includes a rod passing through the medical device and forcing the medical device against a portion of the roll which is not immersed in the reservoir of the coating material.

In an exemplary embodiment of the invention, the roll includes a cylinder and a sleeve disposed over the cylinder, the sleeve including the recessed pattern on a surface facing away from the cylinder.

In an exemplary embodiment of the invention, the roll is at least partially porous so as to allow for impregnation of the coating material.

In an exemplary embodiment of the invention, the struts of the stent contact the roll only within the recessed pattern.

Another medical device coating apparatus according to an exemplary embodiment of the present invention includes: (i) one of a plate and cylinder having one of an opening and a pattern of openings matching a pattern of a medical device to be coated; and (ii) one of a squeegee and blade configured to move relative to a first surface of the one of the plate and the cylinder and force a medical device coating material through one of the opening and the pattern of openings on to the medical device.

In an exemplary embodiment of the invention, the fixture is configured to maintain the medical device in rolling contact with a second surface of one of the plate and the cylinder.

In an exemplary embodiment of the invention, a surface speed of the medical device is the same as a surface speed of one of the plate and the cylinder.

In an exemplary embodiment of the invention, one of the squeegee and the blade is disposed within the cylinder.

In an exemplary embodiment of the invention, one of the plate and the cylinder include a coated wire mesh and the pattern of openings includes uncoated areas of the wire mesh.

In an exemplary embodiment of the invention, the pattern of openings in the plate or cylinder matches a strut pattern of the stent.

DETAILED DESCRIPTION

Figure 1:
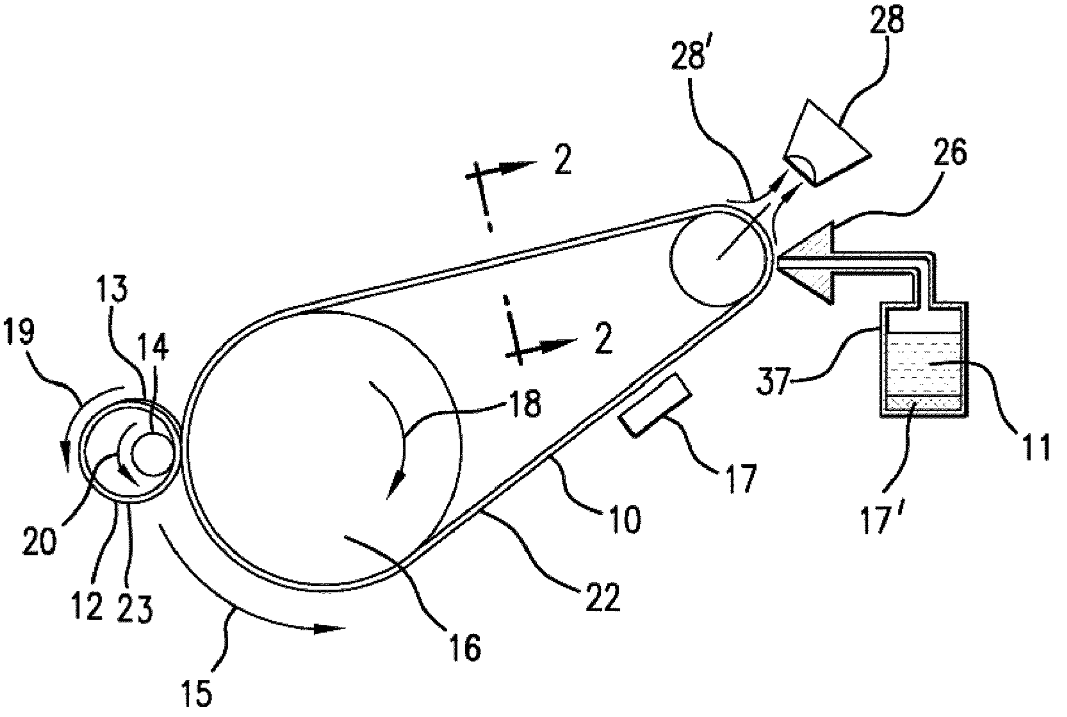
FIG. 1 is a schematic diagram of an exemplary system according to the present invention including a coating material impregnated ribbon.

FIG. 1 illustrates a medical device, such as a stent 12, in rolling contact with a ribbon 10. The ribbon 10 is impregnated with a stent coating material 11, for example, including a therapeutic agent, which is applied to the stent 12 upon contact with the ribbon 10. Stent coating material 11 forms a coating, such as a therapeutic coating 13, on the stent 12 as it rolls in the direction of arrow 15 along the ribbon 10. Coating 13 is shown only along a portion of the circumference of stent 12 which has rolled against ribbon 10. As stent 12 completes its first rotation coating 13 will extend around the entire circumference of stent 12. Pin 14 may rotate along arrow 20 and, thus causes the stent 12 to rotate in the direction of arrow 19 and roll along the ribbon 10 in the direction of arrow 15. Alternatively, an outer diameter of pin 14 may match an inner diameter of stent 12 and pin 14, similar to cylinder 16, may rotate in place without the stent 12 moving in the direction of arrow 15. The term impregnate as used herein refers generally to the absorption of a sufficient amount of coating material by the ribbon 10 (or other application device) so as to form a coating of desired thickness on the medical device being coated. The term ribbon 10 as used herein refers to any material capable of holding coating material 11 and then imparting it onto the stent 12 via contact with stent 12.

Ribbon 10 may be made from a pliable flexible material and, thus, may conform to an outer surface of the stent 12. Cylinder 16 may rotate, for example, in a clockwise direction as shown by arrow 18. Pin 14 and cylinder 16 force the stent 12 in contact with the ribbon 10 at a predetermined pressure. Pin 14 and cylinder 16 may be connected to drives/motors or may be rotated manually. The thickness of the coating 13 formed on the stent 12 may be controlled by regulating the thickness of a porous layer 24 at a ribbon surface 22 and by regulating the pressure at which pin 14 and cylinder 16 squeeze the ribbon 10 and stent 12 together. The temperature and humidity may be controlled to alter the surface tension and viscosity of the coating material 11 thereby improving wet-ability. To improve surface wet-ability, the surface 23 of stent 12 may also be prepared, for example, by plasma, corona, laser treatment, micro bead or sand blasting, chemical etching, etc.

Figure 2:
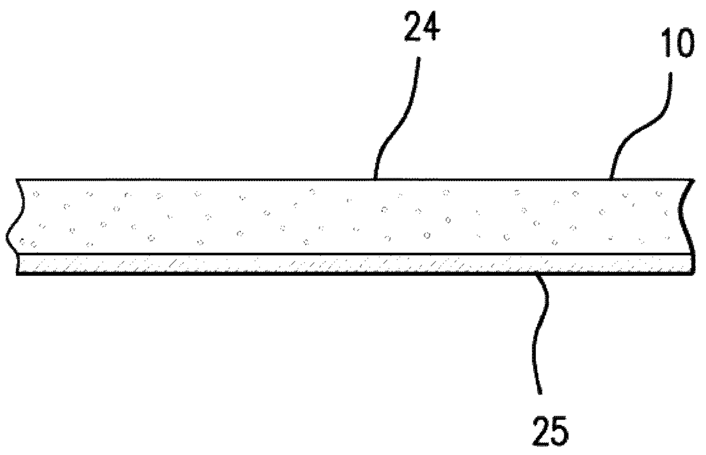
FIG. 2 is a transverse cross section along lines 2-2 of the ribbon in FIG. 1.

FIG. 2 illustrates a cross section of the ribbon 10 along lines 2-2 in FIG. 1. Ribbon 10 may include any material capable of holding coating material 11 for application to the stent 12. Ribbon 10 may be porous along an entire width or may have a porous layer 24 over, for example, a reinforcement underlayer 25, as illustrated in FIG. 2.

Figure 3:
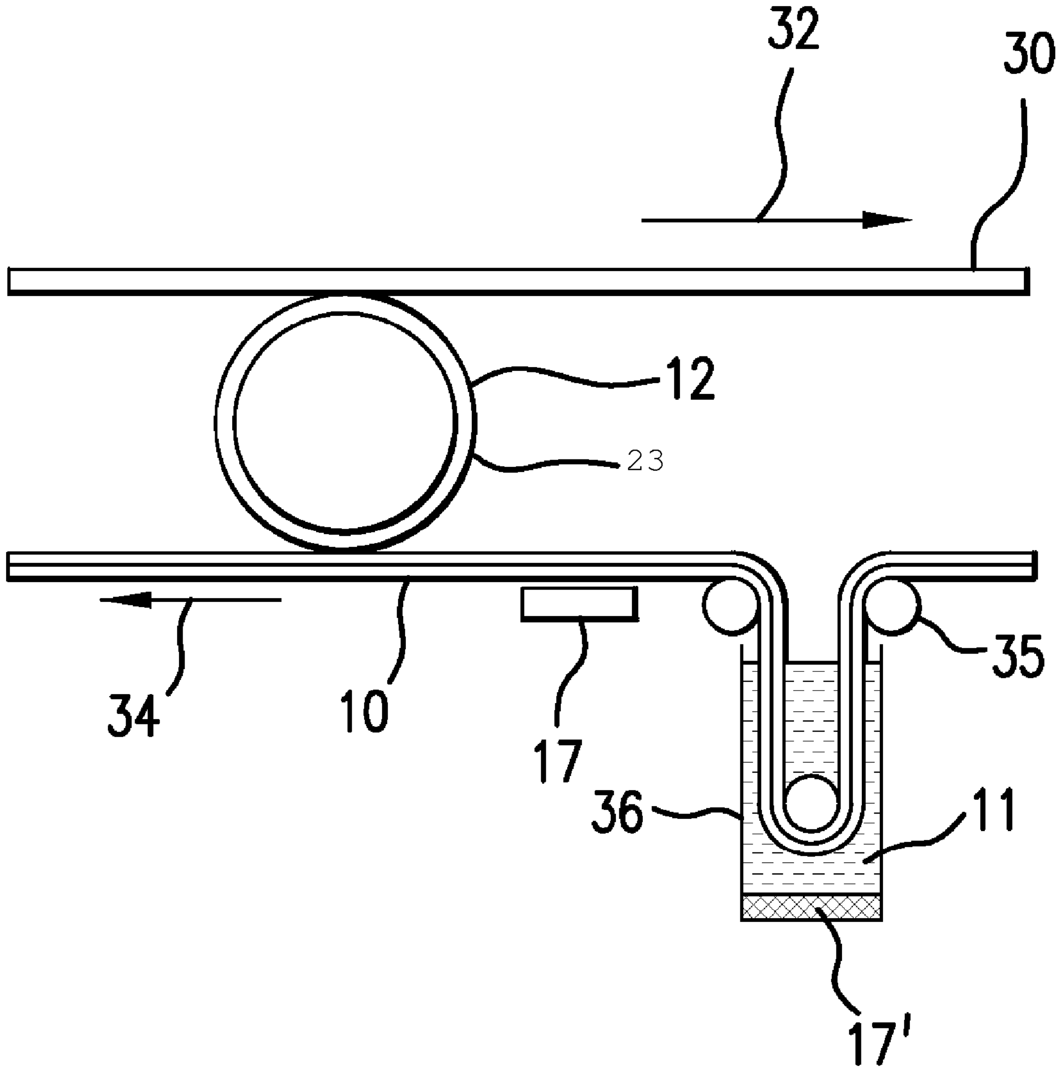
FIG. 3 is a schematic diagram of an exemplary system according to the present invention including a coating material impregnated ribbon.

Coating material 11 may be applied to the ribbon 10 by spraying the coating material 11, stored in a reservoir 37, on the ribbon 10 using injector 26 or by passing the ribbon through a reservoir 36 of the coating material 11, as shown in FIG. 3. Reservoir 37 may be kept closed and/or chilled to reduce evaporation. A vacuum 28 may be used to evacuate all gas from the porous layer 24 of the ribbon 10 prior to impregnation of the ribbon 10 with coating material 11. Gas may be drawn in the direction of arrows 28' into the vacuum 28. Arrows 28' indicate the direction gas drawn from the ribbon 10 takes towards the vacuum 28. The injector 26 may apply the coating material 11 to the ribbon 10 at different concentrations across the ribbon 10 so as to apply different drug doses along a width or length of the stent 12. For example, a lower concentration of coating material may be applied to the ends of the stent 12, which may result in a more favorable therapeutic effect. This could be beneficial as endothelial cells are known to proliferate more readily at ends of the stent 12. A controller may be used to control the spray pattern and coating parameters of the injector 26 and to control the rotation of the stent 12.

The stent 12 may also be rolled on the ribbon 10 using a stent drive belt 30, as illustrated in FIG. 3. As can be seen in FIG. 3, drive belt 30 is moved along arrow 32. Ribbon 10 is moved, for example, by wheels 35, in the opposite direction along arrow 34 after passing through bath 36 of coating material 11. Stent 12 may rotate in place by driving ribbon 10 and drive belt 30 at the same speed or may be driven at a different speed to effect a translation of the stent 12. The drive belt 30 and ribbon 10 may include a low durometer layer to allow it to conform around any irregularities in the stent wall.

In an alternative exemplary embodiment, the stent 12 may also be held in place and a ribbon 10, for example, pre-impregnated with coating material 11 may be wrapped around the stent 12 so as to transfer coating material 11 to the stent 12. The ribbon 10 may be fixed at one end and, for example, a mechanical arm or other known clamping device holding an opposite end of the ribbon 10 may wind around the stent 12 until its outer surface is entirely coated. The ribbon 10 may also be wrapped and unwrapped manually.

The ribbon 10 may be heated using a heater 17 or may include an embedded heating element so as to facilitate the coating process. The coating material reservoirs 36, 37 may also be heated using a heater 17'. Heat may be used to alter a surface tension and viscosity of the coating material 11 to increase wet-ability.

The use of a ribbon 10 to coat a stent has various advantages. For example, the ribbon allows coating of only the outside surface of a stent, which is the surface that faces the vessel wall on deployment. Avoiding coating the inside surface of a stent is desirable in certain instances and avoids wasting coating and/or reduces the dissemination of the coating or therapeutic into the lumen (e.g., the bloodstream). Also, compared to certain spray processes which can result in a low percentage of the dispersed coating material actually adhering to the stent (low transfer efficiency), in the ribbon method as described, the material that leaves the ribbon becomes coated on the stent. This avoids wasting coating material, which can be expensive. Also, the ribbon transfer method does not require any spray forces to be applied to the coating, allowing some sensitive coatings, including those containing bio-molecular therapeutics, to be utilized. As described above, the ribbon can apply different concentrations or types of coatings to different areas of the stent. The ribbon has elasticity to conform to the stent surface, resulting in a relatively consistent coating as compared to some prior art processes.

Figure 4:
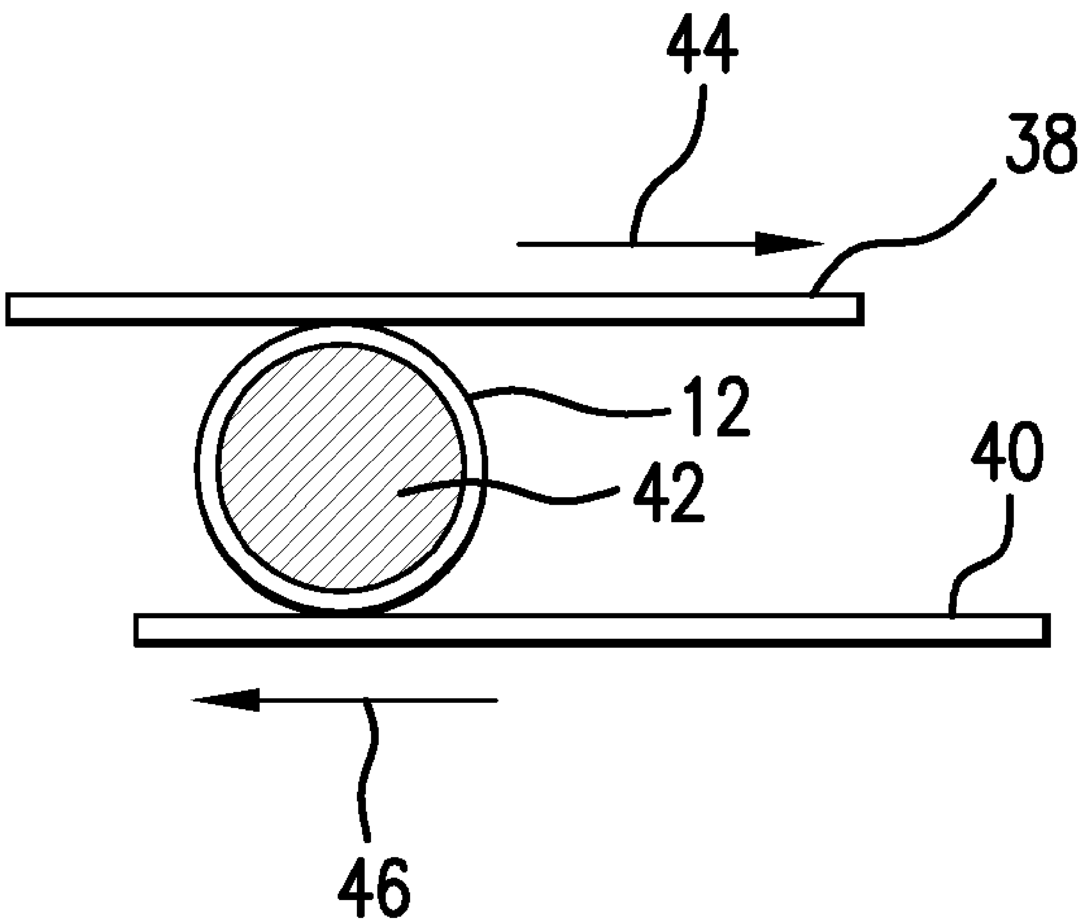
FIG. 4 illustrates a side view of a system for correcting bends in the stent strut.

If desired, prior to coating, stent 12 may be processed to remove any irregularities in the stent wall, e.g., bent struts, so as to assure a true cylindrical outer surface. As can be seen in FIG. 4, the stent 12, disposed over a pin 42, may be rolled between a pair of rigid plates 38 and 40, for example, made from steel. The plates 38, 40 may be moved in opposite directions along arrows 44 and 46 and may squeeze the stent 12 at a pressure sufficient to remove irregularities from the stent wall. Also, the stent 12 may be 'crimped' onto the pin 42 using, for example, the crimping apparatus for crimping stents onto balloons described in U.S. patent application Ser. No. 6,360,577, herein incorporated by reference in its entirety.

Figure 5:
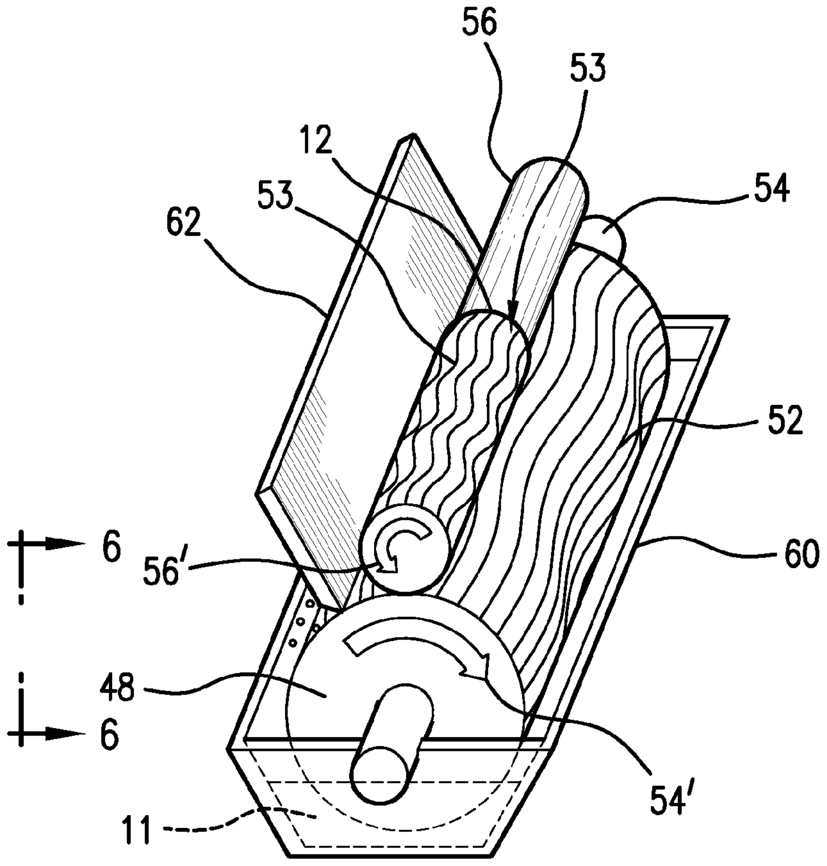
FIG. 5 is a schematic diagram of an exemplary system according to the present invention including a coating material impregnated gravure roll.
Figure 6:
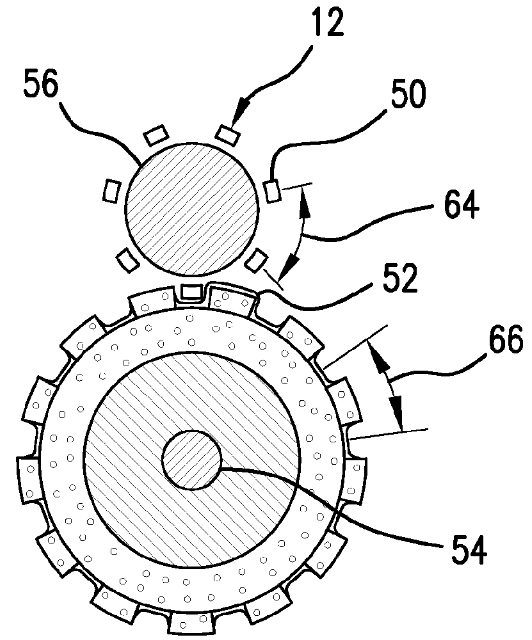
FIG. 6 is a transverse cross section along lines 6-6 of the roll and stent of FIG. 5.
Figure 6A:
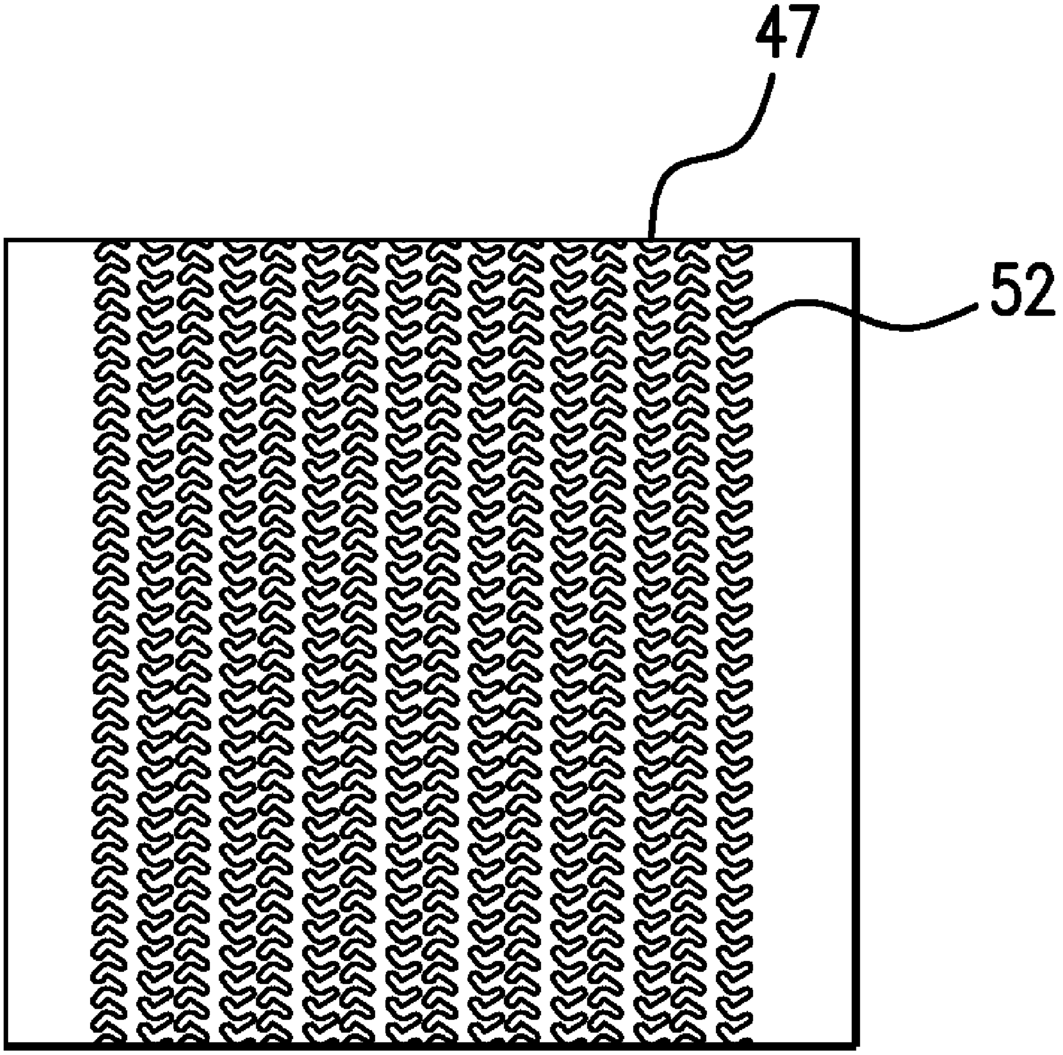
FIG. 6A is a top view of the gravure roll sleeve shown cut longitudinally and flattened.

In an alternative embodiment, an outer surface of the stent 12 may also be coated using a gravure roll 48, as illustrated in FIG. 5. Gravure roll 48 includes a recessed pattern 52 matching the stent pattern 53. As illustrated, the stent struts 50 have a wavy or sinusoidal pattern but any type of stent may be coated. The term strut is intended to mean any structural component defining the stent 12. In the case of a braided stent, for example, the struts are braided wires. Stent 12 may also be made from a piece of metal tubing having a pattern of cutouts, in which case the struts are formed by the remaining wall of the tubing. The stent pattern 53 may be engraved in a sleeve 47 which may be disposed over the roll 48 or the pattern may be engraved in the roll 48 itself. FIG. 6A illustrates a portion of sleeve 47 cut lengthwise and forming a planar sheet so as to most clearly illustrate the recessed pattern 52. The term engraved as used herein applies to all methods for applying the stent pattern 53 to the roll 48, including, for example, molding the roll 48 so as to have the stent pattern 53 on an outside surface, removing material from the outer surface so as to engrave the stent pattern 53 on the roll 48, building up the stent pattern 53 on an outer surface of the roll 48 by setting additional material consistent with the stent pattern 53, etc. The roll 48 may also have a plastically deformable pliable layer which takes on an exact imprint of the stent 12 as it is rolled against it. In use, a stent being coated rolls against the imprinted pliable layer and fits exactly into its imprint on the roll. The imprinted pliable layer may be flattened and reused on another stent. This type of custom roll is useful for coating very flexible and delicate stents whose struts are easily bent and for coating those stents having a large variation, e.g., in a given production batch, resulting from the manufacturing process (the struts are bent in a circumferential or longitudinal direction while still maintaining a cylindrical outer surface). Similar to the roll 48, ribbon 10 of FIG. 1 may also include a recessed pattern 52.

Roll 48 and stent 12 may be rotated on shafts 54, 56 along arrows 54', 56', respectively, and may be manually rotated or connected to a drive for automated rotation. Roll 48 may be partially immersed in a reservoir 60 of the coating material 11. A doctor blade 62 may be used to remove excess coating material 11 from the roll 48. As can be seen in the cross sectional view of the roll 48 and stent 12 illustrated in FIG. 6 taken across lines 6-6 in FIG. 5, a diameter of rod 56 matches an inner diameter of stent 12 and is positioned adjacent roll 48 such that stent 12 contacts roll 48 and one or more struts 50 of stent 12 fit in a portion of recessed pattern 52. For clarity, the reservoir 60 and doctor blade 62 are not shown in FIG. 6. The pattern spacing 64 on the stent 12 matches the pattern spacing 66 on the roll 48.

The use of a gravure roll to coat a stent has various advantages. For example, as with the ribbon, the gravure roll allows coating of only the outside surface of a stent and has a high transfer efficiency. The gravure roll can apply different concentrations or types of coatings to different areas of the stent. In addition, the gravure roll arrangement avoids coating material webbing between the stent struts 50 and provides for a high material transfer efficiency. Further, use of the roll 48 provides for a low shear process, which is especially useful for shear sensitive coating materials.

Figure 7:
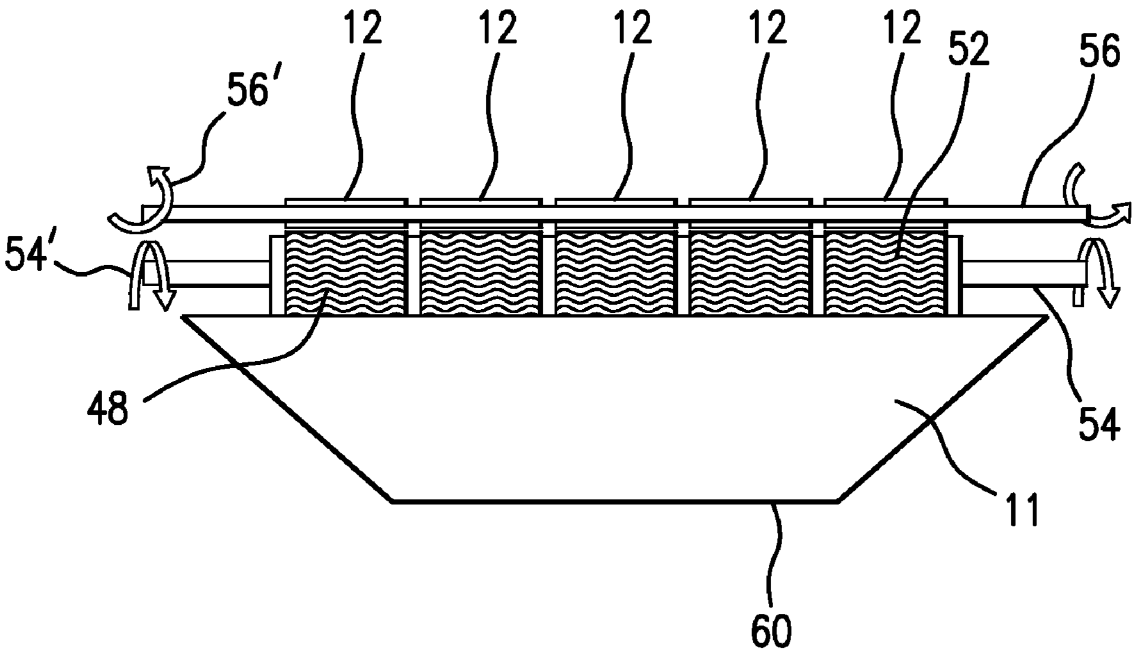
FIG. 7 is a schematic diagram of an exemplary system according to the present invention including a coating material impregnated gravure roll configured to coat multiple stents simultaneously.
Figure 8:
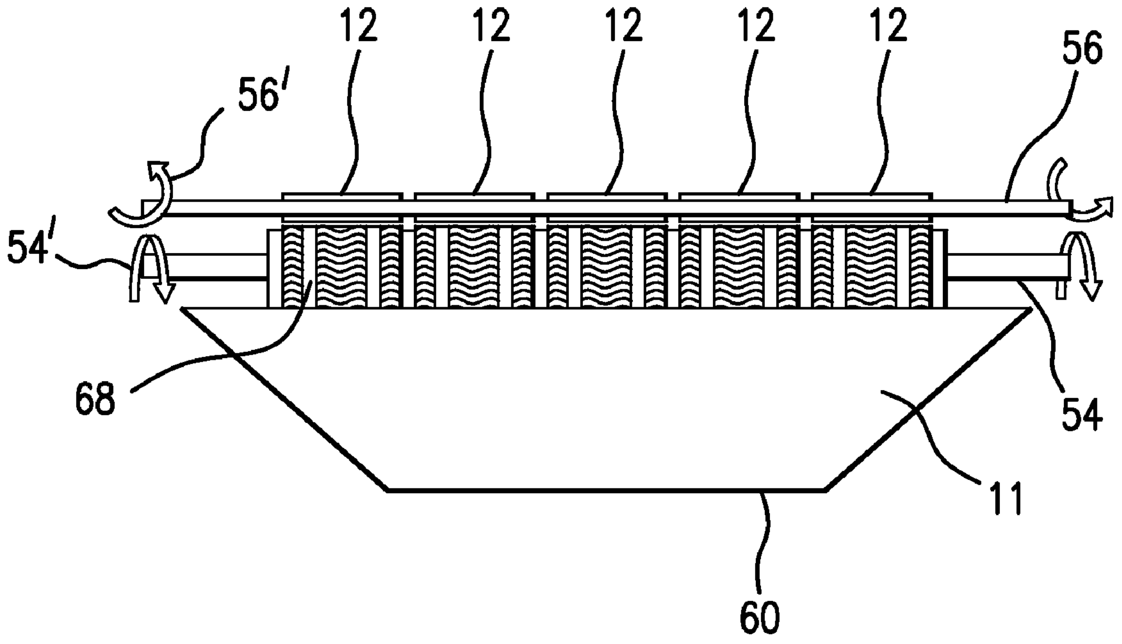
FIG. 8 is a schematic diagram of the system illustrated in FIG. 7 where the roll includes a plurality of engraved rings.
Figure 9:
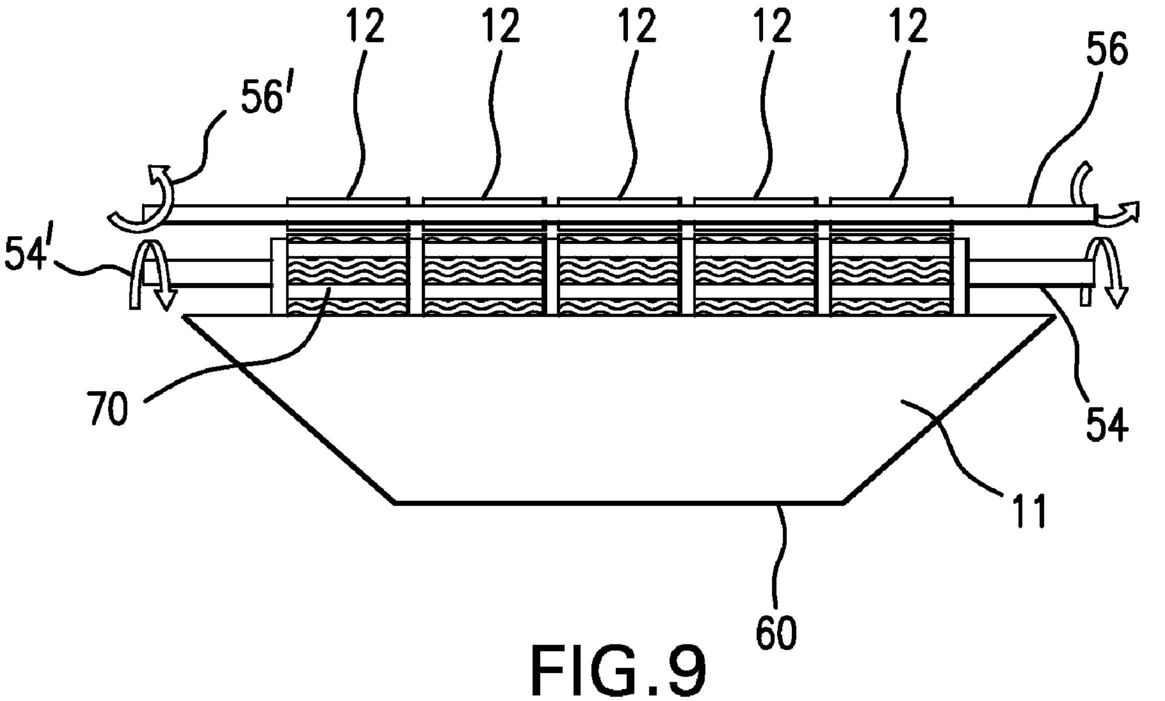
FIG. 9 is a schematic diagram of the system illustrated in FIG. 7 where the roll includes a plurality of longitudinal strips.

A plurality of stents 12 may be coated simultaneously, as illustrated in FIG. 7. Multiple stents 12 are mounted on shaft 56 and the roll 48 includes multiple sets of recessed patterns 52, one for each stent 12. As illustrated in FIGS. 8 and 9, the recessed patterns 52 may include recessed rings 68 and longitudinal strips 70, which result in uncoated sections in the corresponding areas on the stent 12. The recessed rings 68 and strips 70 have a radial depth larger than a thickness of the stent 12. The result is a stent 12 that has only rings or longitudinal strips coated, by the remaining portions of the roll 48.

In an alternative exemplary embodiment, the roll 48 may be pre-impregnated with coating material 11 and may roll around the stent 12, which may be fixed. Alternatively, the roll 48 may be fixed and the stent 12 may be rolled around an outer surface of the roll 48.

Figure 10:
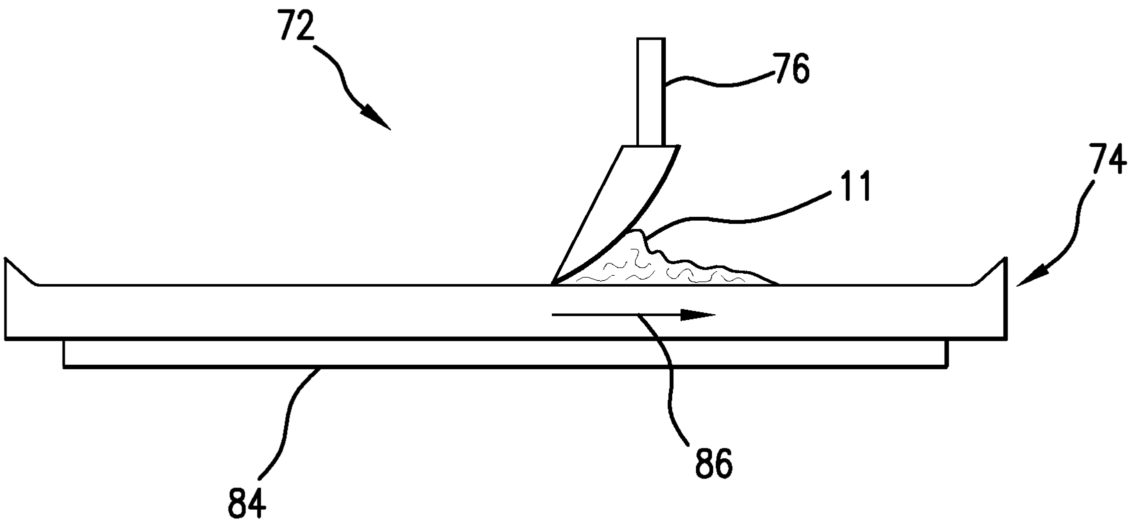
FIG. 10 is a schematic diagram of an exemplary system according to the present invention including a wire mesh for screen printing a planar medical device.
Figure 11:
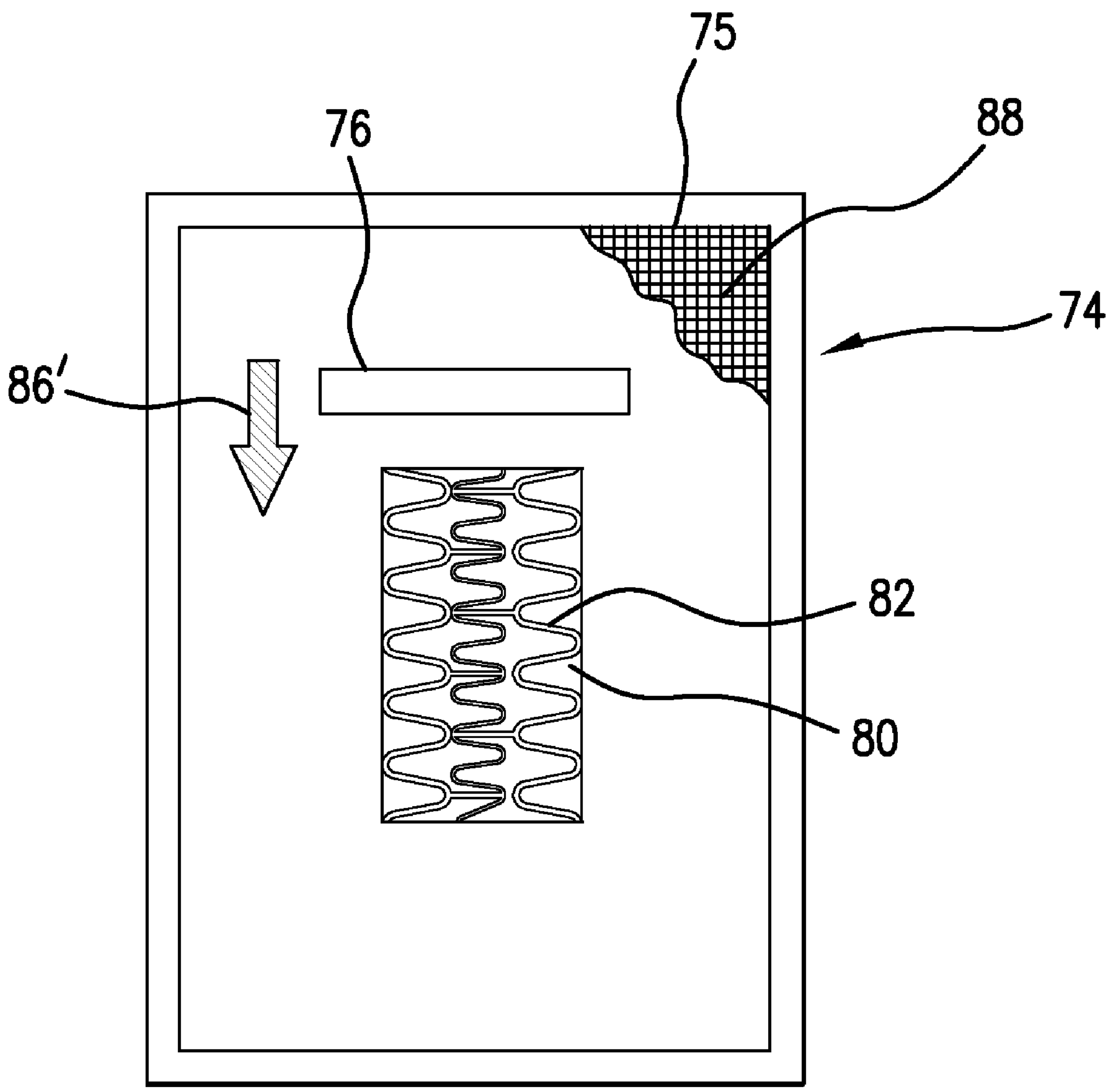
FIG. 11 is a top view of the screen mesh illustrated in FIG. 10.

In accordance with another alternative embodiment, FIG. 10 illustrates a screen printing machine 72 including a screen 74 and a squeegee 76, which may be used to print planar and cylindrical medical devices. As can be seen in the top view of FIG. 11, screen 74 includes coated closed sections 80 and uncoated open sections 82, which match the pattern of a medical device to be coated, such as that of stent 12. Alternatively, open sections 82 can may be replaced with a regular shaped opening, e.g., rectangular, that is large enough to contain the required number of rotations of the stent 12.

The screen 74 may be prepared by coating a wire mesh 75, including wires 88, with a UV curable emulsion. A transparent sheet with a printed pattern, for example, matching the stent pattern 53, may be laid over the wire mesh 75 and the curable emulsion may be cured hardening the curable material everywhere on the screen 74 but for the areas covered by the printed stent pattern 53. The uncured emulsion may be washed away leaving a pattern of openings or uncoated open sections 82 in the screen 74 matching stent pattern 53. Alternatively, screen 74 may be replaced with a plate having cut-outs corresponding to the stent pattern 53. The cut-outs may be generated, for example, using a precision laser cutting tool, by etching, or any other suitable process.

Figure 12:
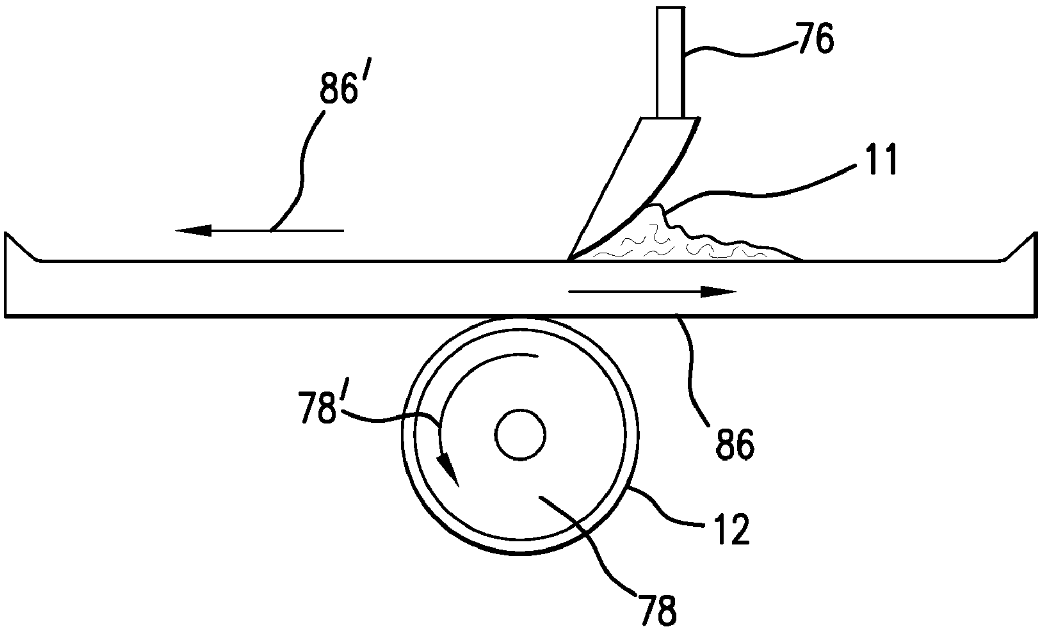
FIG. 12 is a schematic diagram of an exemplary system according to the present invention including a wire mesh for screen printing a cylindrical medical device.

To coat substrate 84, as illustrated in FIG. 10, the squeegee 76 may be moved along arrows 86 relative to the screen 74 so as to force coating material 11 through openings 82. To print on a cylindrical medical device, such as stent 12, stent 12 may be mounted on an impression cylinder 78, as illustrated in FIG. 12. Impression cylinder 78 may rotate counterclockwise along arrow 78', for example, while the screen 74 is moved along arrow 86' and squeegee 76 is moved along arrow 86. A surface speed of the stent 12 and the screen 74 may be equal so as to assure that struts 50 of the stent 12 fall directly beneath openings 82 to receive coating material 11. Struts 50 of stent 12 may be aligned with the openings 82 manually, using a vision system, or using a fixture in mesh with the screen 74 through a suitable gear train. The coating material 11 may be thixotropic in nature so that its viscosity is reduced under the shearing action of the squeegee 76 and the screen 74 and once again increases after being deposited on the stent 12. A thickness of the coating 13 formed on the stent 12 may be controlled by adjusting a diameter of wires 88. Further, a coating material flow rate may be controlled by adjusting a density of the wire mesh 75.

Figure 13:
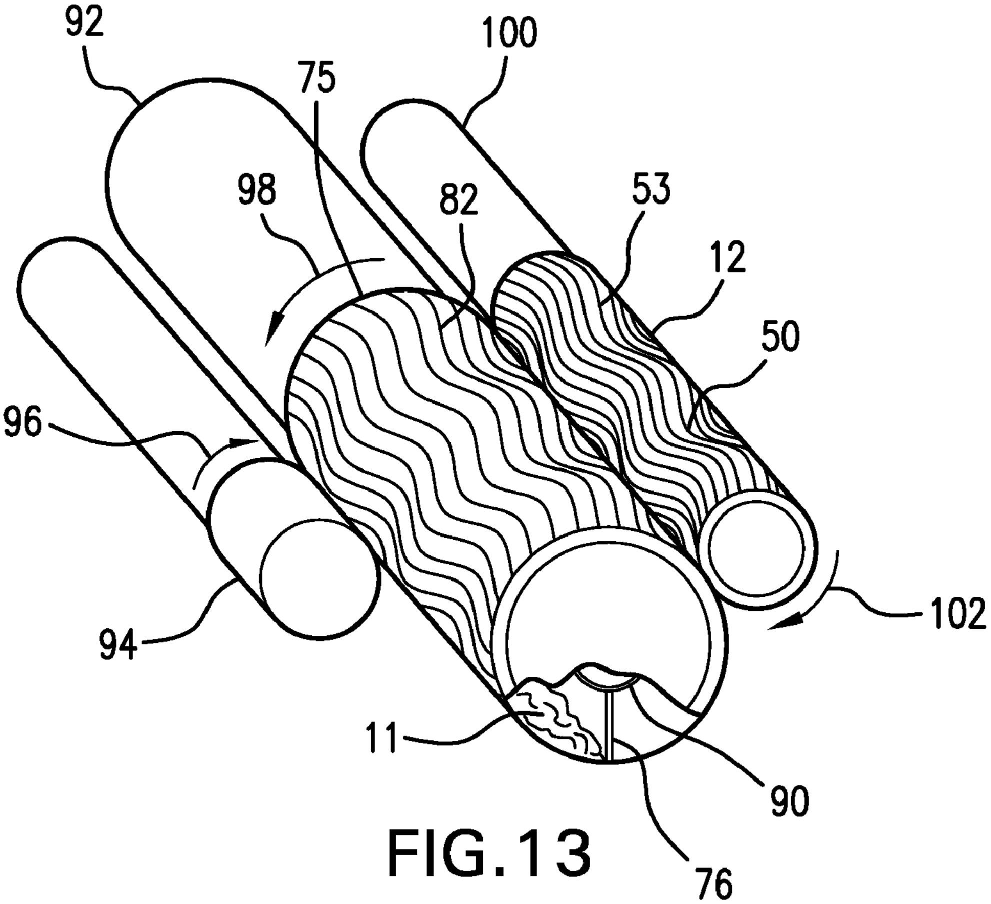
FIG. 13 is a schematic diagram of an exemplary system according to the present invention including a cylindrical screen printer.

For higher speed screen printing, the squeegee 76 and a coating material reservoir 90 may be disposed within screen 75, which is rolled into a cylinder, as illustrated in FIG. 13. Screen 75 is disposed about a fixed support shaft 92 to which squeegee 76 and coating material reservoir 90 may be secured. Multiple squeegees may be disposed within screen 75 to increase throughput. Cylinder 94 may rotate, for example, clockwise in the direction of arrow 96 and may be used to rotate screen 75 in a counterclockwise direction in the direction of arrow 98. Rod 100 may be used to rotate stent 12 in the direction of arrow 102. As screen 75 and stent 12 rotate stent, struts 50 are lined up with openings 82 such that coating material 11 released from coating material reservoir 90 is forced through openings 82 directly onto stent struts 50.

The use of a screen coating process to coat a stent has various advantages. For example, as with the ribbon and gravure roll, the screen allows coating of only the outside surface of a stent and has a high transfer efficiency. The screen process can apply different concentrations or types of coatings to different areas of the stent. In addition, the screen process avoids coating material webbing between the stent struts. Further, the screen process is a low shear process, useful for shear sensitive coating materials.

As used herein, the term "therapeutic agent" includes one or more "therapeutic agents" or "drugs". The terms "therapeutic agents", "active substance" and "drugs" are used interchangeably herein and include pharmaceutically active compounds, nucleic acids with and without carrier vectors such as lipids, compacting agents (such as histones), viruses (such as adenovirus, adeno-associated virus, retrovirus, lentivirus and α-virus), polymers, hyaluronic acid, proteins, cells and the like, with or without targeting sequences.

The therapeutic agent may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl)ethyleneglycol-N,N,N',N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomino linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; inhibitors of heat shock proteins such as geldanamycin; angiotensin converting enzyme (ACE) inhibitors; beta-blockers; bAR kinase (bARKct) inhibitors; phospholamban inhibitors; and any combinations and prodrugs of the above.

Exemplary biomolecules include peptides, polypeptides and proteins, including fusion proteins with molecular weights up to and above 200 kDa; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; anti-restenosis agents; and monoclonal antibodies. Nucleic acids may be incorporated into delivery systems such as, for example, vectors (including viral vectors), plasmids or liposomes.

Non-limiting examples of proteins include serca-2 protein, monocyte chemoattractant proteins ("MCP-1") and bone morphogenic proteins ("BMPs"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPs are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNAs encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, lipids and compounds having a molecular weight of less than 100 kD, inflammatory agents, and immune system modulators. A non-limiting example of an inflammatory agent is interleukin-1 and a non-limiting example of an immune system modulator is interferon beta-1a.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative ($Lin^-$) cells including $Lin^-CD34^-$, $Lin^-CD34^+$, $Lin^-cKit^+$, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, $G_o$ cells, endothelial cells, adult cardiomyocytes, fibroblasts, smooth muscle cells, adult cardiac fibroblasts +5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Any of the therapeutic agents may be combined to the extent such combination is biologically compatible.

Any of the above mentioned therapeutic agents may be incorporated into a polymeric coating on the medical device or applied onto a polymeric coating on a medical device. The polymers of the polymeric coatings may be biodegradable or non-biodegradable. Non-limiting examples of suitable non-biodegradable polymers include polystyrene; polyisobutylene copolymers and styrene-isobutylene-styrene block copolymers such as styrene-isobutylene-styrene tert-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHYDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent/therapeutic agent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating is typically from about 1 to about 50 microns thick. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

Non-limiting examples of medical devices according to the present invention include catheters, guide wires, balloons, filters (e.g., vena cava filters), stents, stent grafts, vascular grafts, intraluminal paving systems, implants and other devices used in connection with drug-loaded polymer coatings. Such medical devices may be implanted or otherwise utilized in body lumina and organs such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like.

While the present invention has been described in connection with the foregoing representative embodiments, it should be readily apparent to those of ordinary skill in the art that the representative embodiments are exemplary in nature and are not to be construed as limiting the scope of protection for the invention as set forth in the appended claims.

What is claimed is:

1. A method for coating a medical device, comprising:

impregnating a ribbon with a coating material at different concentrations across the ribbon; and contacting a medical device and the ribbon so as to coat an outer surface of the medical device with the coating material at different amount across at least one of a length and width of the medical device.

2. The method of coating a medical device of claim 1, wherein contacting the medical device and the ribbon is achieved by at least one of (i) rolling the medical device against the ribbon, (ii) rolling the ribbon against the medical device, (iii) rolling the medical device and ribbon against each other, and (iv) wrapping the ribbon around the medical device.

3. The method for coating a medical device of claim 1, further comprising controlling a thickness of the coating material applied to the medical device by regulating a thickness of a porous layer at a surface of the ribbon contacting the medical device.

4. The method of coating a medical device of claim 2, wherein the medical device rolls in place.

5. The method of coating a medical device of claim 2, wherein the ribbon is moved by rolling a cylinder against it.

6. The method of coating a medical device of claim 1, further comprising the preliminary step of drawing gas out of the ribbon prior to impregnating the ribbon with the coating material.

7. The method of coating a medical device of claim 1, wherein the ribbon is at least partially porous as to allow for impregnation of the coating material.

8. The method of coating a medical device of claim 1, wherein the ribbon is impregnated by spraying the coating material to the ribbon.

9. The method of coating a medical device of claim 2, wherein a surface speed of the ribbon and the medical device are different.

10. The method of coating a medical device of claim 1, further comprising the step of heating at least one of the ribbon and the coating material.

11. The method of coating a medical device of claim 1, wherein the medical device is a stent.

12. The method of coating a medical device of claim 11, further comprising the preliminary step of disposing the stent about a pin and rolling the stent between opposing plates.

* * * * *